US00PP19876P2

(12) United States Plant Patent
Austin

(10) Patent No.: US PP19,876 P2
(45) Date of Patent: Mar. 31, 2009

(54) ***ROSA HYBRIDA* SHRUB NAMED 'AUSBERNARD'**

(50) Latin Name: *Rosa hybrida*
Varietal Denomination: AUSbernard

(75) Inventor: David C.H. Austin, Wolverhampton (GB)

(73) Assignee: David Austin Roses Ltd., Wolverhampton (GB)

( * ) Notice: Subject to any disclaimer, the term of this patent is extended or adjusted under 35 U.S.C. 154(b) by 0 days.

(21) Appl. No.: 12/001,153

(22) Filed: Dec. 10, 2007

(30) Foreign Application Priority Data

Oct. 16, 2007 (GB) ..... AFP5/2099

(51) Int. Cl.
*A01H 5/00* (2006.01)

(52) U.S. Cl. ..... Plt./108

(58) Field of Classification Search ..... Plt./108
See application file for complete search history.

*Primary Examiner*—Kent L Bell
(74) *Attorney, Agent, or Firm*—Kauth, Pomeroy, Peck & Bailey LLP

(57) ABSTRACT

A variety of rose plant of the shrub class, named 'AUSbernard' is disclosed. The 'AUSbernard' rose is a plant suitable for repeat flowering production having deep crimson blooms, a strong Old Rose fragrance and a broad bushy growth.

1 Drawing Sheet

Classification:
The present invention relates to a new *Rosa hybrida* shrub.
Variety denomination:
The new plant has the varietal denomination 'AUSbernard'.

ORIGIN OF INVENTION

This invention relates to a new and distinct variety of shrub rose plant named 'AUSbernard', which was originated by crossing two unnamed, unpatented varieties of *Rosa hybrida.*

BACKGROUND OF THE INVENTION

The primary objective of this breeding was to produce a very healthy repeat flowering variety having deep crimson blooms with a strong fragrance and broad bushy growth.

SUMMARY OF THE INVENTION

Among the features which distinguish the new variety from other presently available and commercial rose cultivars known to the inventor is the following combination of characteristics: deep crimson blooms with a strong old rose fragrance and broad bushy growth.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSbernard' may be asexually propagated by budding and grafting. The budding and grafting successfully occurred on the plant/rootstock *Rosa* cv. 'Dr. Huey' in the United States and on the plant/rootstock *Rosa dumetorum* cv. 'Laxa' in the United Kingdom.

COMPARISON WITH PARENTS

The new rose may be distinguished from its seed parent, by the following combination of characteristics: whereas the parent has smaller blooms with fewer petals, 'AUSbernard' produces a much larger plant. The new variety is classified as a *hybrida* rose with a broad growing habit.

The new variety may be distinguished from its pollen parent, by the following combination of characteristics: whereas the pollen parent bears smaller pink blooms, 'AUSbernard' bears large size flowers of deep crimson.

COMPARISON WITH THE CLOSEST COMMERCIALLY AVAILABLE CULTIVAR

The closest commercially available cultivar to the new variety is the 'AUSromeo' (U.S. Plant Pat. No. 13,993). The new rose may be distinguished from the 'AUSromeo' variety by the following combination of characteristics: the 'AUSromeo' has more petals and larger blooms compared to 'AUSlofty', which has smaller leaves and more prickles.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (2001) except where common terms of color definition are employed.

DESCRIPTION OF THE NEW VARIETY

The following description is of 2 year-old rose plants of the new variety grown outdoors in Albrighton, Britain in the month of August. Phenotypic expression may vary with environmental, cultural and climatic conditions, as well as differences in conditions of light and soil.

Flower characteristics:

*Blooming habit.*—Recurrent. The number of blooms per plant during the growing season is profuse, but there are too many to count.

*Bud.*—Size: About 3 cm long and 3 cm in diameter when the petals start to unfurl. Form: The bud form is globular (with pointed top). Color: When sepals first divide, the bud color is Red-Purple Group 60B with irregular patches of Yellow-Green Group N144D. When half blown, the upper sides of the petals are Red-Purple Group 59A, and the lower sides of the petals are Red-Purple Group 59C. Calyx: Shape: (from above) irregularly rounded. Length: 3 cm. Diameter: 4.5 cm. Sepals: Arrangement: Regular. Color: Upper Surface: Greyed-Green Group 194B. Lower Surface: Yellow-Green Group 144A. Length: 2.5 cm. Width: 0.9 cm. Shape: Subulate. Margin: Glandular Surface texture: Upper Surface: Slightly pubescent. Lower Surface: Smooth, glossy. Number: There are three normally appendaged sepals. There are 2 unappendaged sepals. Apex: The typical and observed sepal apex has medium extensions. Margin: The typical and observed unappendaged sepals have glandular edges. Receptacles: Color: Yellow-Green Group 144A. Shape: Funnel. Size: Small, about 0.7 cm×0.7 cm. Surface: Smooth. Peduncle: Length: Medium, averaging about 7.5 cm. Diameter: Average diameter is about 3 mm. Surface: Prickly. Color: Yellow-Green Group 144C overlaid with Greyed-Red Group 181B. Strength: Normal.

*Blooms.*—Size: Large, average open diameter is about 9.5 cm. Depth: Average bloom depth is about 4 cm. Borne: In clusters of 5–7 blooms having corymb shaped inflorescence. Stems: Strength: Normal, average length is about 35 cm. Diameter: 4 mm. Form: When first open, bloom is cupped. Permanence of bloom: flattens.

*Petalage.*—Number of petals under normal conditions: 70–75. Color: The upper sides of the petals are Red-Purple Group 59A. The reverse sides of the petals are Red-Purple Group 64A. The base of the petals is Red-Purple Group 59A. Fragrance: Strong. Character of fragrance: Old Rose.

*Petals.*—Texture: Smooth, velvety. Size: Width: 3.3 cm. Length: 4.2 cm. Surface: Smooth. Shape: Round [outer] and Obovate [inner]. Margin: Most are entire, though towards center some are notched. Apex Shape: Rounded. Base Shape: Obtuse. Form: Incurved; tips slightly recurved. Arrangement: Slightly quartered and regularly arranged without being imbricated. Petaloids: Number: 6. Color: Petal: Red-Purple Group 64A; Anther: Yellow-Orange Group 15A; Filament: Yellow-Orange Group 15A. Length: Petal: 15 mm. Anther: 3 mm. Filament: 8 mm. Width: Petal only: 10 mm Shape: Irregular. Margin: Irregular. Persistence: Petals drop off cleanly before drying. Lastingness: On the plant: fair, about 4–5 days. As a cut flower: about 3–4 days.

*Reproductive parts.*—Stamens: Number: 50. Length: 9 mm. Anthers: Length: 2 mm. Color: Yellow-Orange Group 15A. Arrangement: Regular around styles mixed with petaloids. Filaments: Color: Yellow-Orange Group 15A. Length: 7 mm. Pollen: Color: Yellow-Orange Group 15A. Pistils: Number: 70. Length: 8–9 mm. Styles: Color: Green-Yellow Group 1C. Length: 7 mm. Stigmas: Color: Yellow-Orange Group 14B and Red-Purple Group 69A. Length: 1–2 mm. Hips: None Observed.

Plant characteristics:

*Plant form.*—Shrub.

*Plant growth.*—Vigorous and bushy.

*Age to maturity.*—Two years.

*Mature plant.*—Height: 0.9 m. Width: 0.75 m.

*Rootstock.*—*Rosa* 'Dr. Huey' for U.S. and *Rosa dumetorum* cv. 'Laxa' for observed plants in the U.K.

*Foliage.*—Number: Leaflets on normal mid-stem leaves: 5 [including terminal leaflet]. Size: Medium, about 13.5 cm long×9.6 cm wide. Quantity: Normal. Number of Leaves per flowering stem: 8–10. Color: New foliage: Upper side: Yellow-Green Group N144A, overlaid with Red-Purple Group 60A. Lower side: Yellow-Green Group N144A overlaid with Red-Purple Group 60A. Old foliage: Upper side: Green Group 137A. Lower side: Green Group 138B.

*Leaflets.*—Size: About 5.3 cm long×3.4 cm wide. Shape: Broadly oval. Base Shape: Rounded. Apex Shape: Acuminate. Texture: Leathery. Edge: Serrated. Serrations: Single. Petiole: Color: Green-Yellow Group 144A. Length: 5 cm. Width: 1.5 mm. Surface Texture: Glandular with some small prickles. Petiole Rachis: Color: Yellow-Green Group 144A. Underside: Smooth. Stipules: Length: 2.8 cm, smooth. Color: Yellow-Green Group 144B. Auricle: Shape: Falcate. Length: 7 mm. Width: 2 mm at base tapering to point. Color: Yellow-Green Group 144B. Vein Color: Yellow-Green Group 144D. Venation Pattern: Reticulate.

*Wood.*—New Wood: Color: Red-Purple Group 60A. Bark: rough [prickly]. Old Wood: Color: Green Group 138A. Bark: rough [prickly].

*Branching habit.*—Number: 4 per main stem. Lateral Branch Dimensions: Length: 35 cm. Diameter: 4 mm.

*Stems.*—Mature Stem: Length: 60 cm. Diameter: 4 mm. Internode Distance: 4.5 cm. The above measurements are all variable, depending on growing conditions in a season. Stem Pubescence Present: No. Color: Green Group 138A.

*Prickles.*—Quantity: On main canes from base: Many. Number per stem length: 40 per 10 cm. On laterals from main canes: Many. Number per stem length: 40 per 10 cm. Form: Linear. Length: 7 mm. Color when young: Greyed-Red Group 178A. Color when mature: Greyed-Orange Group 176C.

*Small prickles.*—Quantity: Main stalk: Many. Number per stem length: 150 per 20 cm. Laterals: Many. Number per stem Length: 150 per 20 cm. Color: When young: Greyed-Red Group 178A. When mature: Greyed-Orange Group 176C.

*Disease resistance.*—Mildew: Resistant to Powdery Mildew and Downy Mildew. Blackspot: Resistant. Rust: Resistant.

*Pest resistance.*—Not tested.

*Winter hardiness.*—Not tested.

*Growing conditions.*—Normal for a garden rose, namely, outdoors in soil.

What is claimed is:

1. A new and distinct variety of rose plant of the shrub class suitable for repeat flower production, substantially as herein shown and described.

* * * * *

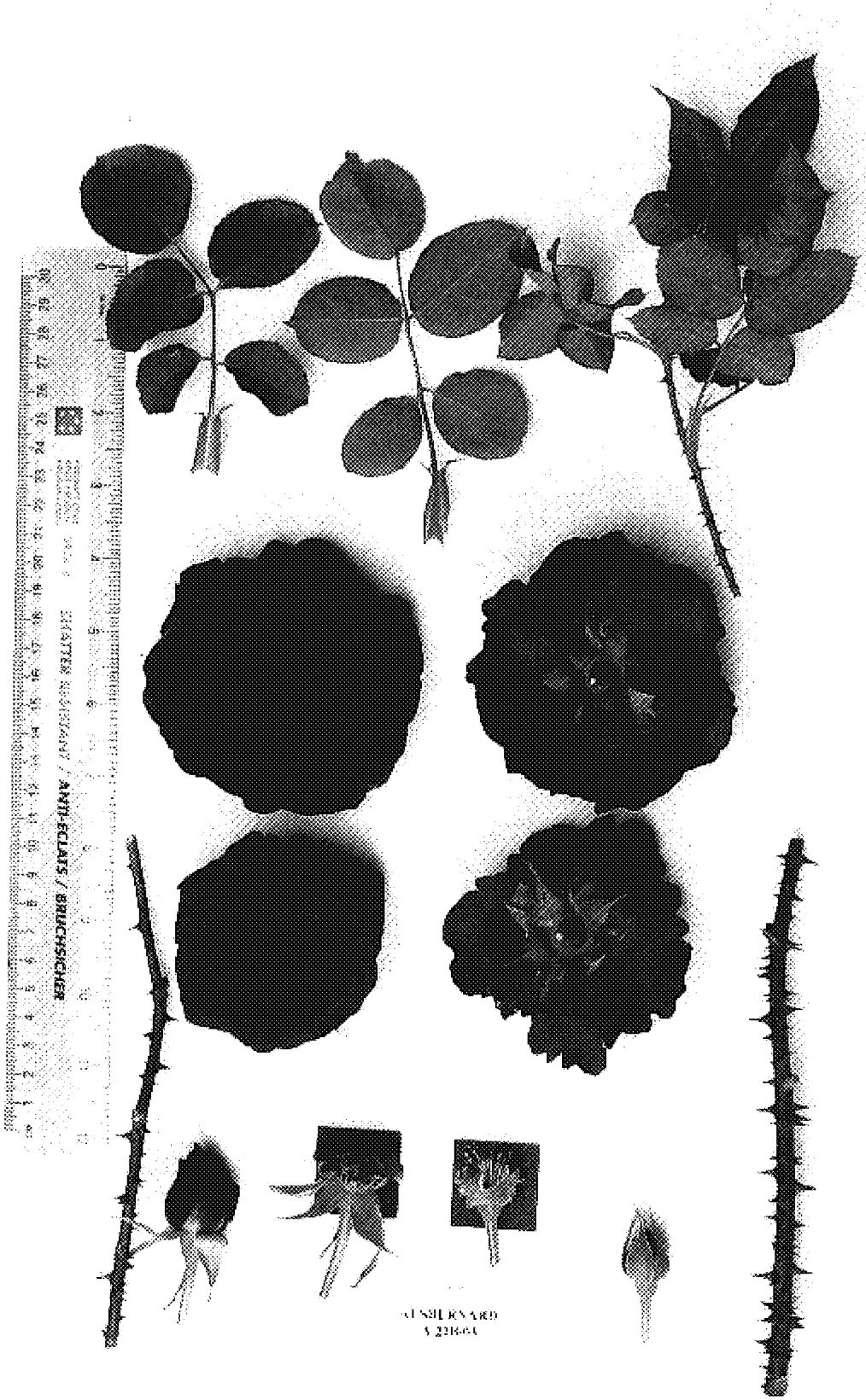
ANTI-ECLATS / BRUCHSICHER
CUSHLEYARD
S 2218-04